(12) United States Patent
Hyer

(10) Patent No.: US 12,741,102 B1
(45) Date of Patent: Sep. 22, 2026

(54) ELECTRO-MECHANICAL INJECTION SITE PREPARATION SYSTEM AND METHOD

(71) Applicant: Jacob Hyer, Apex, NC (US)

(72) Inventor: Jacob Hyer, Apex, NC (US)

( * ) Notice: Subject to any disclaimer, the term of this patent is extended or adjusted under 35 U.S.C. 154(b) by 647 days.

(21) Appl. No.: 18/303,427

(22) Filed: Apr. 19, 2023

Related U.S. Application Data

(60) Provisional application No. 63/332,430, filed on Apr. 19, 2022.

(51) Int. Cl.

| | |
|---|---|
| ***A61M 5/42*** | (2006.01) |
| ***A61H 21/00*** | (2006.01) |
| ***A61H 23/02*** | (2006.01) |
| ***A61N 1/36*** | (2006.01) |

(52) U.S. Cl.
CPC ............. *A61M 5/422* (2013.01); *A61H 21/00* (2013.01); *A61H 23/02* (2013.01); *A61N 1/36071* (2013.01); *A61H 2201/10* (2013.01); *A61H 2201/5005* (2013.01); *A61M 2205/054* (2013.01); *A61M 2205/582* (2013.01)

(58) Field of Classification Search
CPC ............ A61M 5/422; A61M 2205/054; A61M 2205/582; A61H 21/00; A61H 23/02; A61H 2201/5005; A61N 1/36071
See application file for complete search history.

(56) References Cited

U.S. PATENT DOCUMENTS

2012/0065487 A1* 3/2012 O'Malley .......... A61B 5/15186 600/583
2016/0045678 A1* 2/2016 Vallero .................. A61H 23/02 607/46
2018/0369064 A1* 12/2018 Baxter ...................... A61F 7/02

* cited by examiner

*Primary Examiner* — Amanda K Hulbert

(74) *Attorney, Agent, or Firm* — Lambert Shortell & Connaughton; David J. Connaughton, Jr.; Justin P. Tinger

(57) ABSTRACT

An electro-mechanical system configured to prepare a site in an oral area to receive a painless injection, whereby the system generates at the site a first vibratory amplitude output for a first period, then generates a first electrical stimulation output in combination with the vibratory amplitude. A user may then inject the site or increase the vibratory amplitude or electrical stimulation intensity prior to injecting at or near the site. The system includes a housing having a pair of extending prongs, by which the vibratory and electrical outputs may be transmitted on to the site. The extending prongs may be rotatable and angled with respect to the housing.

12 Claims, 10 Drawing Sheets

Using Electro-Mechanical Device

ELECTRO-MECHANICAL INJECTION SITE PREPARATION SYSTEM AND METHOD

TECHNICAL FIELD

The present invention relates to preparing sites prior to and during the use of an injection device, such as a syringe carrying a medicament to be delivered to a user.

BACKGROUND

When preparing a site for injecting a medicament into it, various methods have been deployed in attempt to minimize the pain or shock to the patient, which at times can cause the patient to have sudden physical reaction that may harm them or the person administering the injection. Some of these methods include using a first topical anesthetic in attempt to numb the injection site, others will slap, pinch or rapidly oscillate the area during the injection. For example, a dentist may grab a part of the patient's cheek and try to oscillate it rapidly while injecting Lidocaine into an oral area. As with the dentist example, if the patient flinches, the needle could cause additional pain or harm to the patient and the dentist could potentially suffer harm as the person administering the shot. As such, the present application seeks to improve upon previous techniques and further mitigate flinching and potential harm by providing a system that better prepares sites for injections.

SUMMARY

In one embodiment, an electro-mechanical system for preparing injection sites comprises: a housing; a vibratory system disposed at least partially within the housing; a power supply connected to the housing; a resilient or rigid arm having a first fork portion and a second fork portion; an electrical stimulation system, wherein a portion of the electrical stimulation includes electrical stimulating areas disposed on each of the first and second fork portions; and at a first set of controls disposed on an outer surface of the housing for operating the vibratory system and the electrical stimulation system.

In a variation of the above embodiment the resilient or rigid arm can be configured to rotate with respect to the housing. The rotation arm(s) may or may not be fixable in a certain position.

In another embodiment, an electro-mechanical system for preparing injection sites, the system comprising: a housing; a vibratory system disposed at least partially within the housing; a power supply connected to the housing; an arm having a first fork portion and a second fork portion; an electrical stimulation system, wherein a portion of the electrical stimulation includes electrical stimulating areas disposed on each of the first and second fork portions; and a set of controls disposed on an outer surface of the housing for operating the vibratory system and the electrical stimulation system.

In a variation to the above embodiment the arm can be configured to rotate with respect to the housing.

The set of controls of the above embodiment can be configured to increase or decrease the vibratory frequency of the vibratory system, as well as increase or decrease the electrical stimulation frequency of the electrical stimulation system. They can also be configured to initiate a first vibratory frequency generated by the vibratory system, and then subsequently initiate a first electrical stimulation frequency generated by the electrical stimulation system. This can be done manually or pre-programmed to be done automatically. For example the controls can cause the vibratory system to change from the first vibratory frequency to a second vibratory frequency. Likewise, they can cause the first electrical stimulation frequency to transition to a second electrical stimulation frequency. Again, manually or automatically.

The vibratory system noted above can be configured to generate a vibration amplitude in a range from 2G to 5G. This generated vibration amplitude of the vibratory system can be sufficient to impart at the first fork portion or second fork portion a vibration amplitude in the range of 1G to 4G.

The vibratory system can generate a frequency in the range of 50 Hz to 300 Hz in the above embodiment.

The first or second electrical stimulation frequency can be pulsed at pulse width range of 180-280 μs.

The electrical stimulation system can deliver between 0 and 2.5 Watts via the electrical stimulating areas disposed on each of the first and second fork portions of the above embodiment.

The electro-mechanical system can be configured such that the activation of the vibratory system and the electrical stimulation system inside a recipient's mouth causes A-beta fibers to activate, thus closing the pain gate from an oral cavity of the recipient's mouth to the recipient's central nervous system.

In another embodiment, a method of preparing a site for injection, comprising the steps of: setting and applying a first vibration amplitude generated by a vibratory system of an electro-mechanical system to the site for injection; setting and applying a first electrical stimulation intensity generated by an electrical stimulation system of the electro-mechanical system to the site for injection; and increasing the first electrical stimulation intensity to a second electrical stimulation intensity that is greater in intensity than the first electrical stimulation intensity, such that the combination of the applied vibration amplitude and the second electrical stimulation intensity are sufficient to reduce the registration or perception of pain associated with an injection needle, and wherein the electro-mechanical system further includes one or more prongs through which to apply the first vibration amplitude and the first and second electrical stimulation intensity to the site for injection.

For the above method, the first electrical stimulation intensity can be greater than 0 W, but less than 2.5 W and wherein the second electrical stimulation intensity can be greater than the first electrical stimulation intensity, but less than or equal to 2.5 W.

In a variation to the above method, the electro-mechanical system is configured to automatically initiate the first electrical stimulation intensity and gradually increase the intensity until the desired second electrical stimulation intensity is achieved over a period of time, and wherein the period of time is programmable.

For the above method, the one or more prongs can be connected to an arm that is configured to rotate about a housing of the electro-mechanical system.

For the above method the electro-mechanical system includes a vibratory system configured to generate a vibratory amplitude having a range of 2G-5G.

Also for the above method, the site for injection can be associated with an oral cavity of a recipient, wherein the vibratory amplitude is applied to the site for injection for a period of greater than 1 second prior to the first electrical stimulation intensity being applied, such that the duration and vibratory amplitude cause a sensory system associated with the recipient's oral cavity to allow for the intensity of the second electrical stimulation intensity to be greater without recipient discomfort than if the recipient were receiving the second electrical stimulation intensity alone.

Of course, the present invention is not limited to the above features and advantages. Those of ordinary skill in the art will recognize additional features and advantages upon reading the following detailed description, and upon viewing the accompanying drawings.

DETAILED DESCRIPTION

Figure 1:
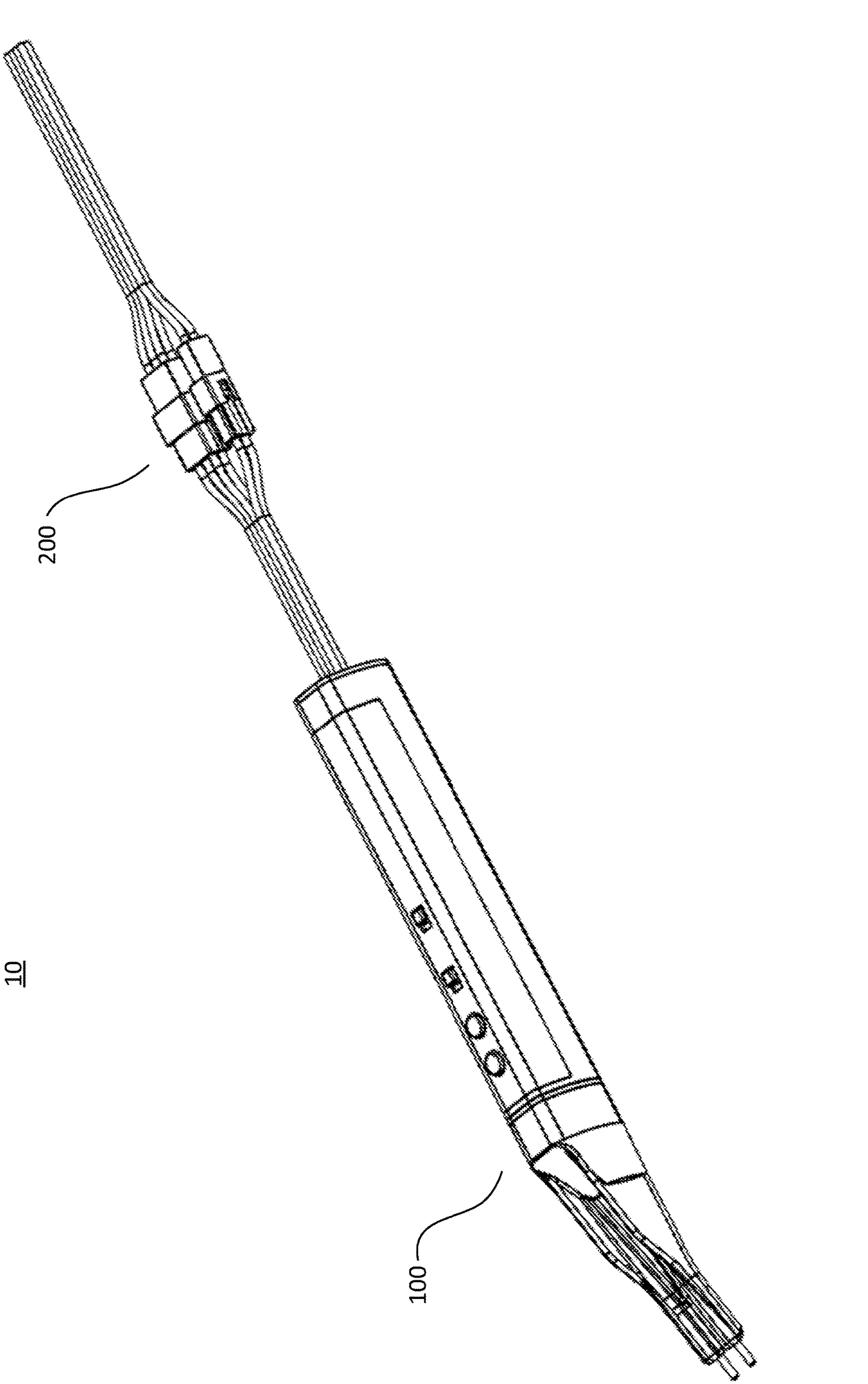
FIG. 1 illustrates a perspective view of an electro-mechanical system including power and communication cords.

Embodiments of the present invention are directed to an electro-mechanical system used to prepare injection sites and methods of using the same.

As noted above, one of the objectives is to reduce pain and sensation of an injection site while administering an injection. This injection site could be anywhere on the human body; however, most of the embodiments and methodologies are derived specifically the mouth or oral areas of a recipient.

There is a Gate Control Theory of Pain that essentially suggests non painful stimulus can override painful stimulus. In other words, neuronal input from non-noxious stimulation closes the gate on the noxious neuronal input to higher levels in the pain.

Teeth, gingival tissue, and mucosa in the oral cavity are innervated with sensory nerve fibers from the fifth cranial nerve (CN V, aka the trigeminal nerve.) The trigeminal nerve's sensory nerve fibers include nociceptive fibers (A-delta and C fibers), and low-threshold mechanoreceptors (LTMs; A-alpha and A-beta fibers.)

The trigeminal nerve projects beyond the trigeminal ganglion to the trigeminal nucleus caudalis in the brain stem. The brain stem is where the spinal cord connects to the brain. This is also where the primary neurons from CN V, synapse onto second order neurons which then project to the thalamus and then higher up towards the cortex.

Although the trigeminal nucleus caudalis is analogous to the substantia gelatinosa of the dorsal horn of the spinal column, it is a different anatomical structure with different physiologic parameters and thresholds related to the blocking of perception of pain using vibration and nerve stimulation. As a result, the applicant has developed a system and methodologies specific to this system using Gate Control Theory principles to override the pain associated with injections in oral areas.

It has been documented that transcutaneous electrical nerve stimulations ('TENS') uses electric current produced by a device to stimulate the nerves. This can be used for various purposes including eliminating pain. TENS and ultra-low frequency TENS can be used to treat TMD (temporomandibular joint dysfunction). In some ways, TENS use can stimulate competing sensory neurons at the pain reception gate as well as stimulate the opiate response.

Vibration and vibrating mechanisms can also have an overwhelming impact on the sensory system, which similar to TENS can overcome or stimulate competing sensory neurons, as well as stimulate the opiate response.

The applicant has identified that by combining the benefits of vibration, and TENS into a single electromechanical system an improved system could be created. The applicant has also identified that the order of operations effects the range to which the two types of stimulation can be operated in, which ultimately leads to maximizing the saturation or overriding of the sensory system associated with the oral cavity, to severely reduce if not eliminate the painful stimulus associated with receiving an oral injection.

The below embodiments and methods utilizing some of the above techniques will further expand on the above noted advantages.

Referring now to FIG. 1, which illustrates a perspective view of an electro-mechanical system 10 including an electro-mechanical device 100 connect to a power and communication system 200.

Figure 2A:
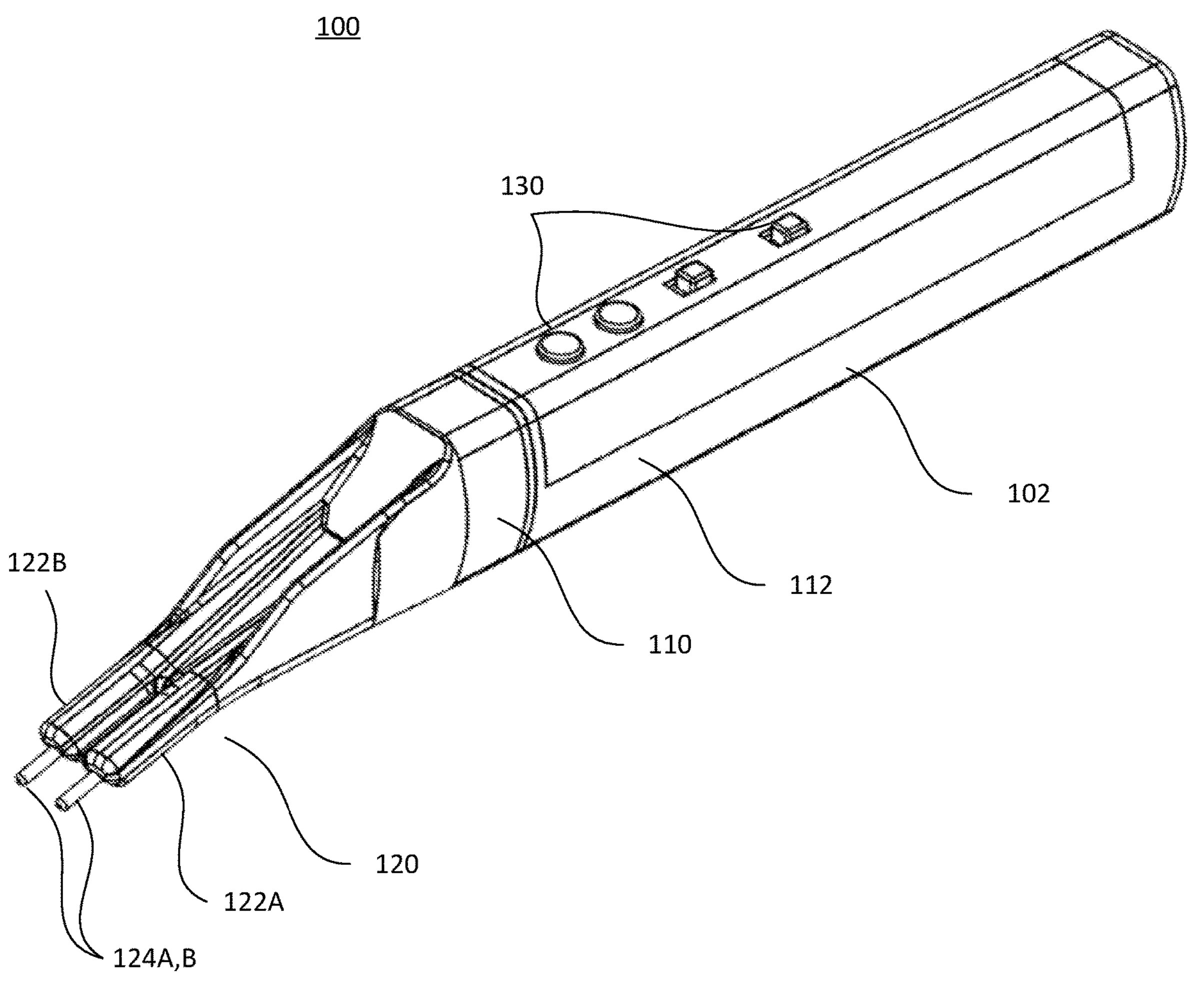
FIGS. 2A-E illustrate various views of the electro-mechanical device of FIG. 1.
Figure 2B:
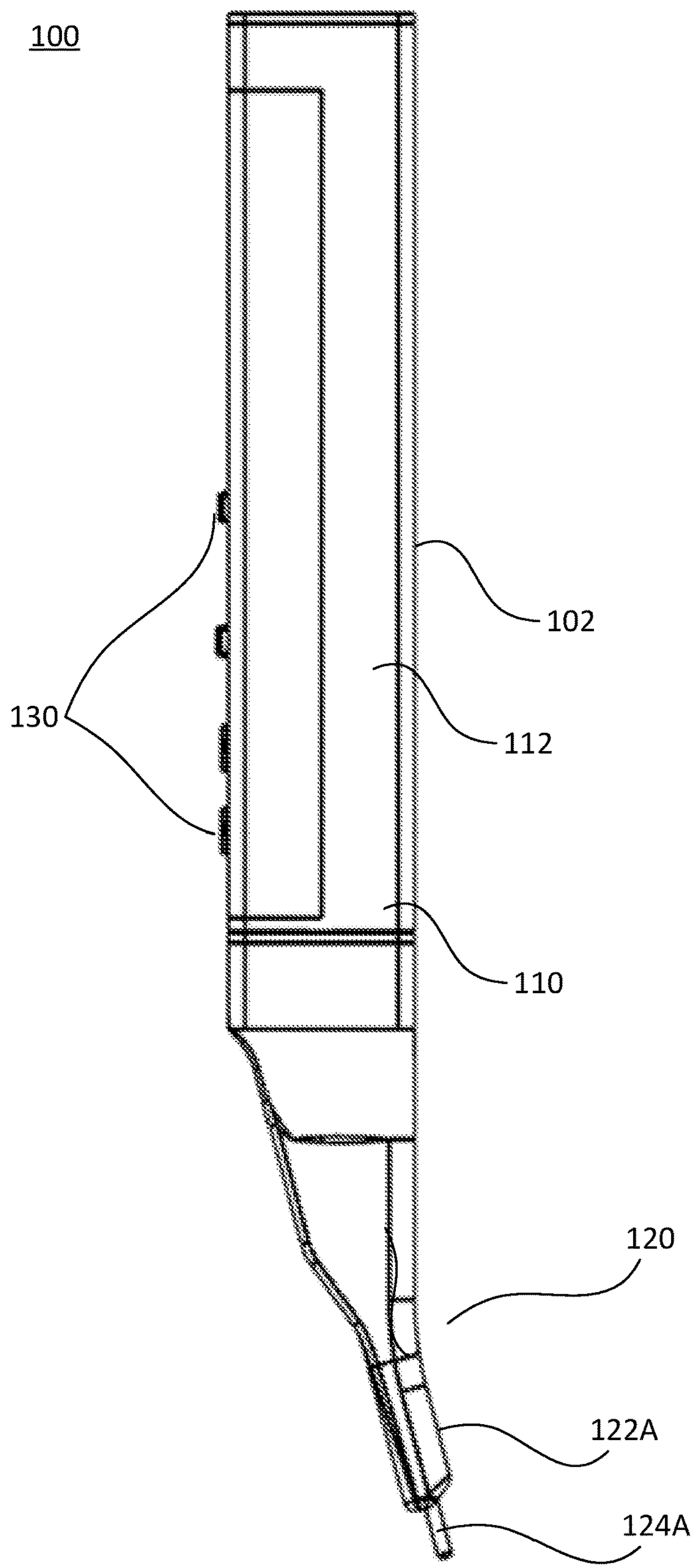
Figure 2C:
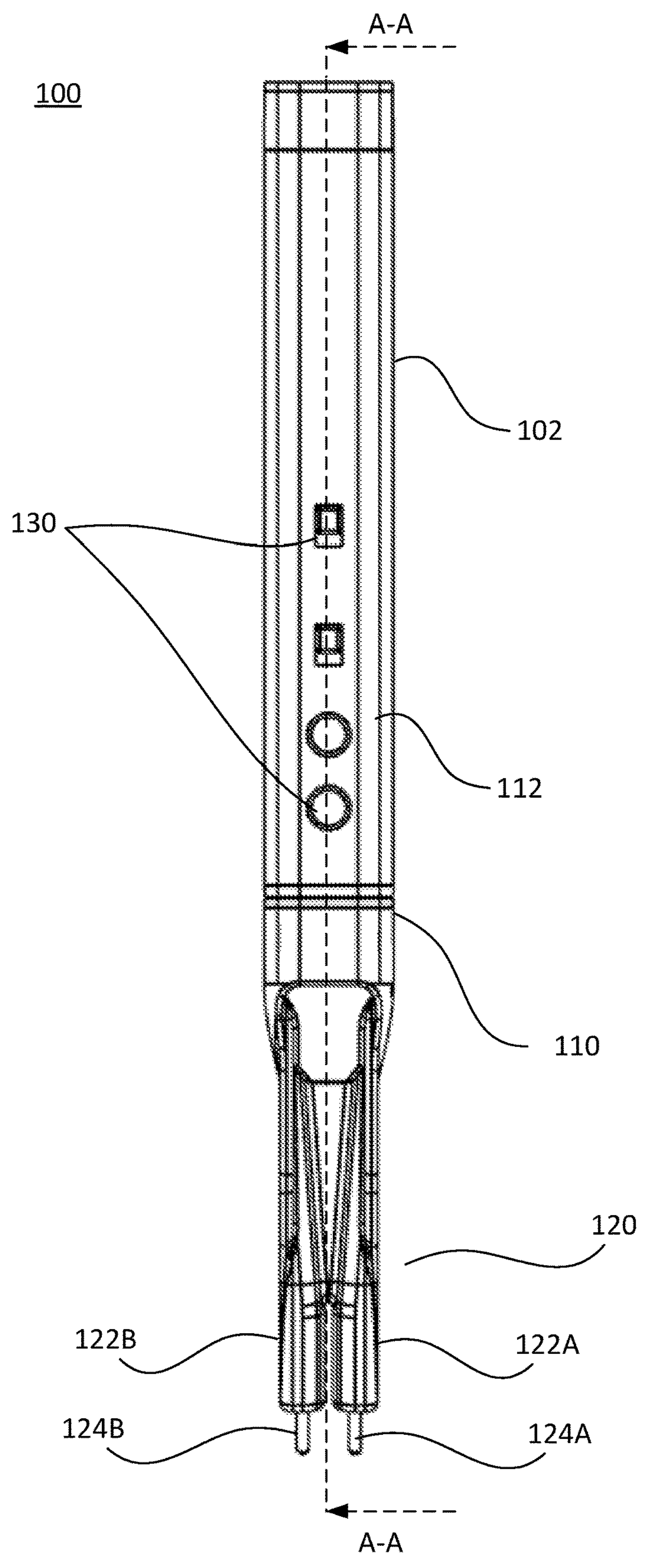
Figure 2D:
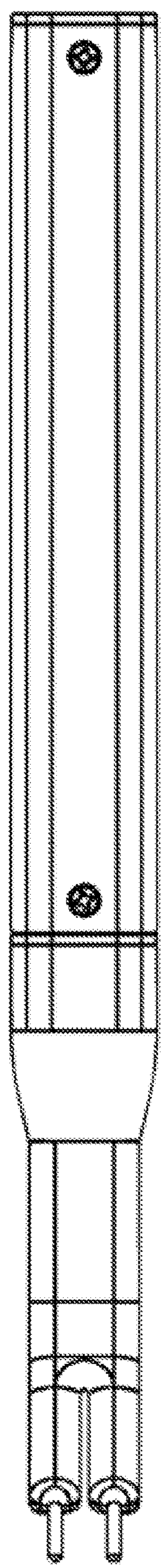
Figure 2E:
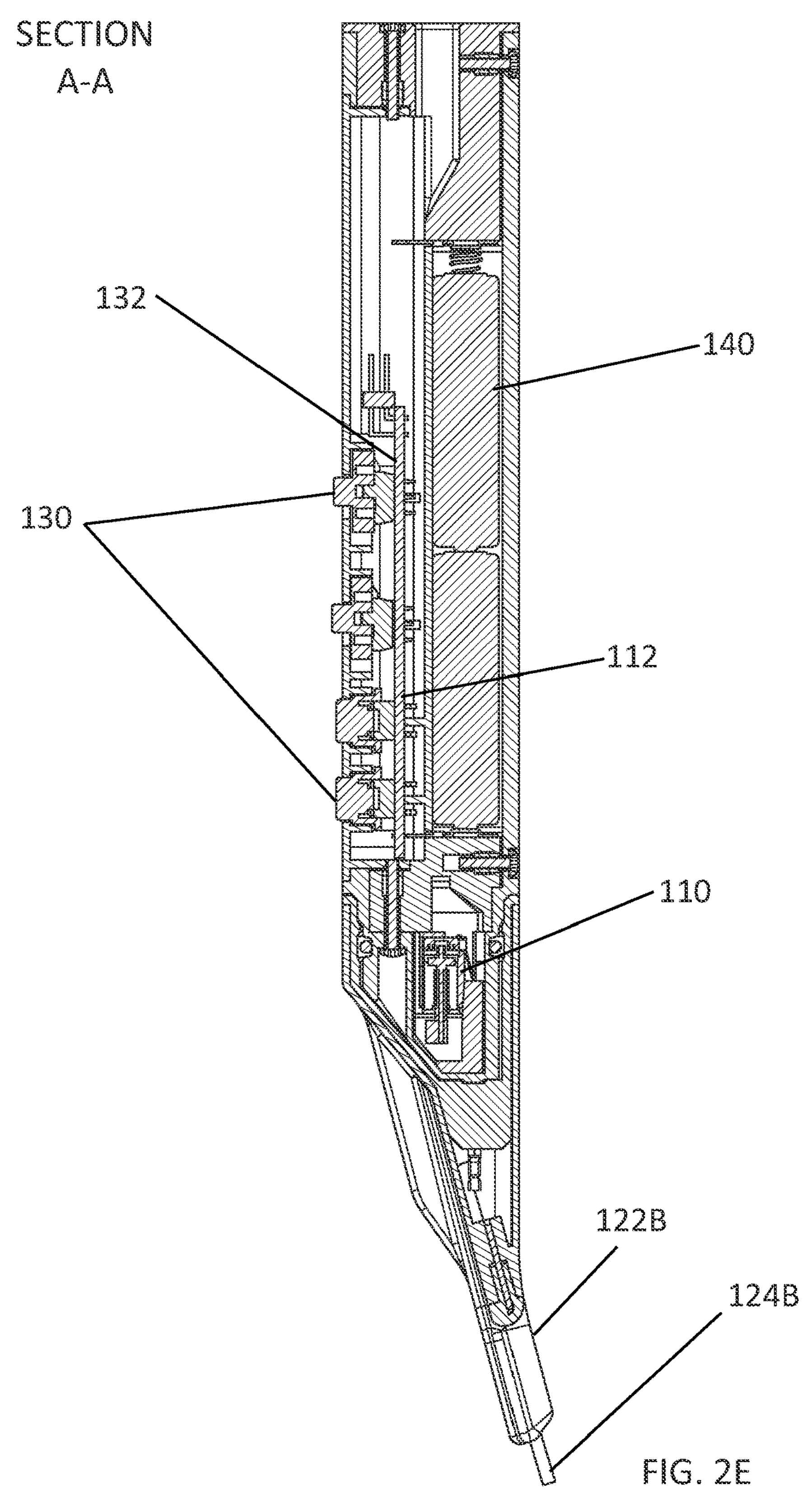

FIGS. 2A-E illustrate various views and features of the electro-mechanical device 100 of FIG. 1. Device 100 includes a housing 102 having a set of controls 130 disposed in a manner to be operated externally about the housing. The set of operating controls 130 can include mechanical, sliding, and even capacitive reacting buttons and switches, which enable a user to operate the device 100. The housing is configured to contain portions of a vibratory system 110 and an electrical stimulation system 112. An arm 120 is connected to one end of the housing 102 and includes a first fork or prong 122A and a second fork or prong 122B. Each of the prongs 122A, B includes an electrical stimulating area 124A and 124B respectively, which can be used to deliver an electrical stimulus to an injection site in an oral area of a recipient. FIG. 2A illustrates a perspective view of device 100, while FIG. 2B illustrates a side view, FIG. 2C illustrates a top view from which cross-sectional view A-A is established and shown in FIG. 2E, and FIG. 2D shows a bottom view.

It should be noted that the electrical stimulating areas 124A, B are generally made from a conductive material, such as a conductive metal.

The vibratory system 110 can more clearly be shown in FIG. 2E. The vibratory system can be configured to generate a vibratory amplitude in a range of 2G to 5G. For those skilled in the vibratory motor art, they will recognize that although G refers to gravity or acceleration, the unit is really meant to reflect the resulting vibratory amplitude for a fixed mass, which is often determined to be 100 g. The reason for this is vibratory motors are almost always connected to another piece of equipment, which information associated with the combination is generally what is sought. However, that would require a calculation specific to each system, so in order to provide customers with a basis for comparison the units are based on a fixed mass. Thus, for purposes of this disclosure the common G unit associated with vibratory motors is adopted.

The position of the vibratory system and the materials, shape and size of the rest of the device 102 effect the vibratory amplitude. As a result, the applicant has developed a device 100 that includes a vibratory system 110 that can generate a 2G to 5G range, which imparts and translates to the first and second fork or prong portions a vibratory amplitude range of 1G to 4G that can be received by the recipient about the injection site area.

The frequency range of the vibratory system can operate in ranges between 5 Hz and 100 Hz, 25 Hz and 150 Hz, 50 Hz and 200 Hz, 50 Hz and 300 Hz, 100 Hz and 300 Hz.

A control board 132 is operatively connected to the set of controls 130 and the vibratory system 110 to modify the vibratory amplitude, frequency, as well as timing. The control board is connected to a power source, such as internal power source 140, which could include battery that could be recharged or directly connected to an external power source.

The electrical stimulation system 112 is also shown in FIG. 2E and which is also operatively connected to the control board 132 draws power from the internal or external power source to create electrical stimulus that is transferred to the oral area of a recipient via the electrical stimulating areas 124A and 124B. The electrical stimulation system can be a TENS unit. The electrical signal frequency system 112 generates can be pulsed with a pulse width range of 10-100 μs, 50-150, 100-300 μs, and preferably 180-280 μs. The intensity or power system 112 can produce a range from 0 W (watts) to 2.5 W. It should be noted that by adjusting the current or voltage of the system, the total Watt output is changed.

As a result of the control board 132, which can receive input from the operating controls 130, the vibratory amplitude output can be activated and adjusted, the electrical stimulation output can be activated and adjusted to cause the A-Beta fibers associated with the sensory system of a recipient's oral area to activate, which activation can result in a saturation of these nonpainful signals being sent through the trigeminal nerve to the trigeminal spinal nucleus caudalis. Higher order nociception projecting neurons, projecting from the nucleus caudalis will be blocked from transmitting pain towards the thalamus and cortex. In other words, this device prevents or blocks the trigeminal nerves A delta or C fibers from transmitting nociception to higher order neurons beyond the nucleus caudalis to the thalamus or the cortex.

Figure 3A:
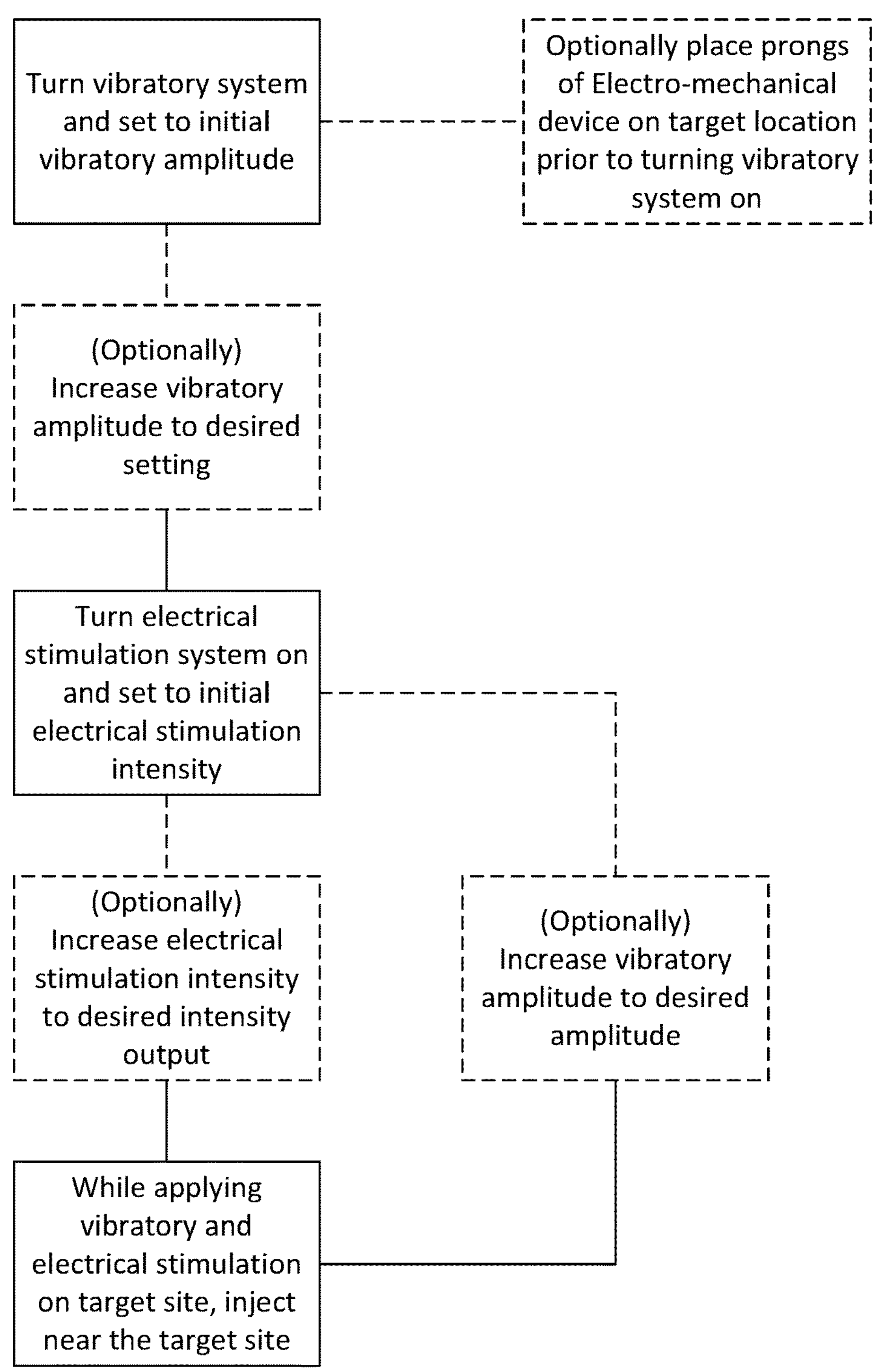
FIGS. 3A-B illustrate flowcharts of methodologies of preparing a site for injection using an electro-mechanical system.
Figure 3B:
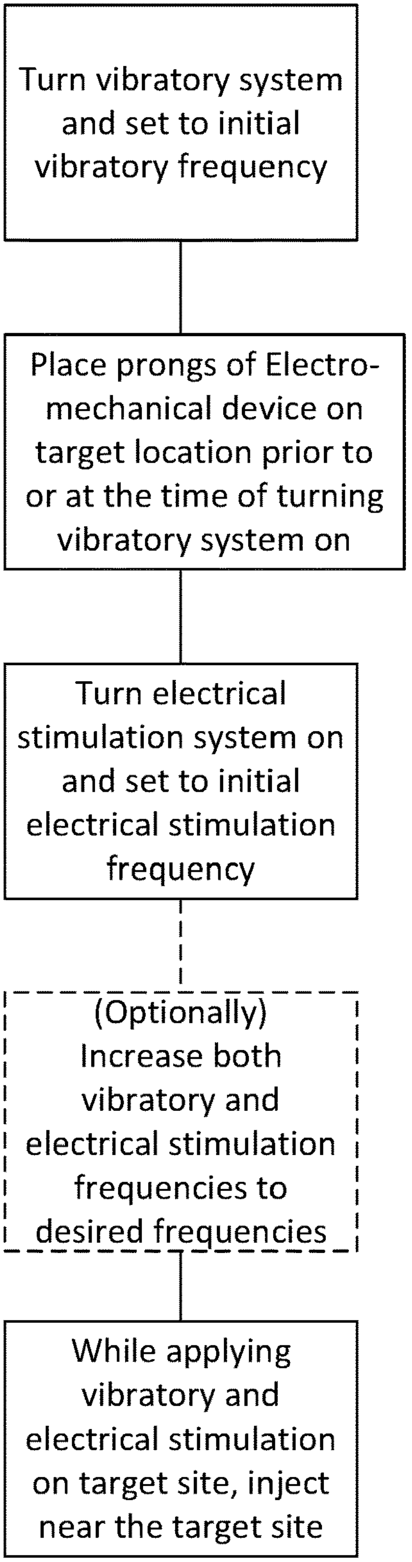

Referring now to FIGS. 3A-B which illustrate flowcharts of methodologies of preparing a site for injection using an electro-mechanical system, such as described above. FIG. 3A illustrates that one of the first steps is to turn the vibratory system on and set the output to an initial vibratory amplitude. Optionally, the user could place the first and second prongs on the desired injection site first and then turn the vibratory system on or this could be done after turning the vibratory system on. If desired the user could then increase the vibratory amplitude output or adjust it downward based on the given circumstances. For example, too much amplitude could have some discomfort, whereas too little might need create the desired intent, which is in combination with electrical stimulation to prevent pain signals from the injection area from being received by the thalamus or cortex. Once the vibratory stimulation is at the desired level, the user can then activate the electrical stimulation system to generate a first electrical stimulation output. This may be sufficient to inject near the targeted injection site. However, in a preferred method, the user starts at a lower electrical stimulation and increases the intensity to a second stimulation output intensity and then injects.

One of the benefits of starting with the vibratory stimulation is that it is a sensation that recipients are more familiar with and it does a good job of beginning to activate the A-Beta Fibers. Another benefit is that it enables the recipient to receive a higher amount of electrical stimulation output. In some testing, it was demonstrated that recipients could handle an increase in electrical stimulation between 20 to 60% greater than using electrical stimulation alone before the intensity of the electrical stimulation was too much and caused discomfort. The increase in electrical stimulation output received by the recipient activates the A-beta Fibers in a manner that completely or almost completely prevents pain from being recognized from an injection near the injection that is being stimulated by both the vibratory and electrical outputs.

Another advantage of the order of these operations and combination is that users, such as dentists, no longer need to provide a topical anesthetic gel prior to injecting another anesthetic such as lidocaine and other commonly used anesthetics in the industry. Topical gels take time to penetrate into the gums to provide the relief of pain from the injecting of lidocaine for example. By decreasing the amount of chair time a patient needs to be there, a resulting increase in the number of patients or procedures a dentist can perform in a given day, thus enabling an opportunity to increase revenue.

Although there exist vibratory only products to be used to prepare oral sites for injection, they all recommend using and allowing the topical gel anesthetic to settle in prior to using the vibratory tool. Thus, they don't save on time, nor do the eliminate the bad-tasting topical gels from their normal dental procedures.

FIG. 3B illustrates a more streamlined methodology of preparing injection sites, again starting with turning the vibratory system, placing the prongs on the injection site, turning the electrical stimulation on, increasing either the vibratory or electrical stimulation outputs and then injecting. As noted above, the preferred methodology includes starting with the desired vibratory setting, having it on the injection site for at least 0.5-1 seconds then starting with an initial electrical stimulation output, increasing that to a second electrical stimulation and finally injecting. This entire process of preparing a site can take less than a minute to prepare the patient for receiving a painless or almost completely painless injection. Of course, there are variations of starting with the electrical stimulation first, and then doing vibration and then increasing electrical stimulation also works. However, it has been determined a better experience involves starting with vibration.

As noted above, the system can be programmed to start with vibration stimulation first for a first period of time, then activate a first electrical stimulation output, then over another period of time increase that first level electrical stimulation output to a second level electrical stimulation output, before finally injecting the site. Once the injection is done the user can then remove or deactivate the system-meaning turning the vibratory and electrical stimulations systems off.

Figure 4A:
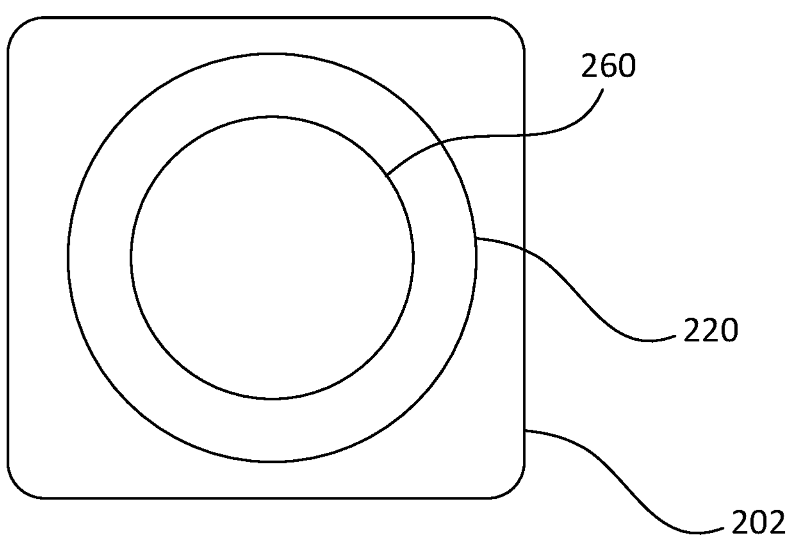
FIG. 4 illustrates various cross-sections illustrating the rotatability of the arm portion of the electro-mechanical system.
Figure 4B:
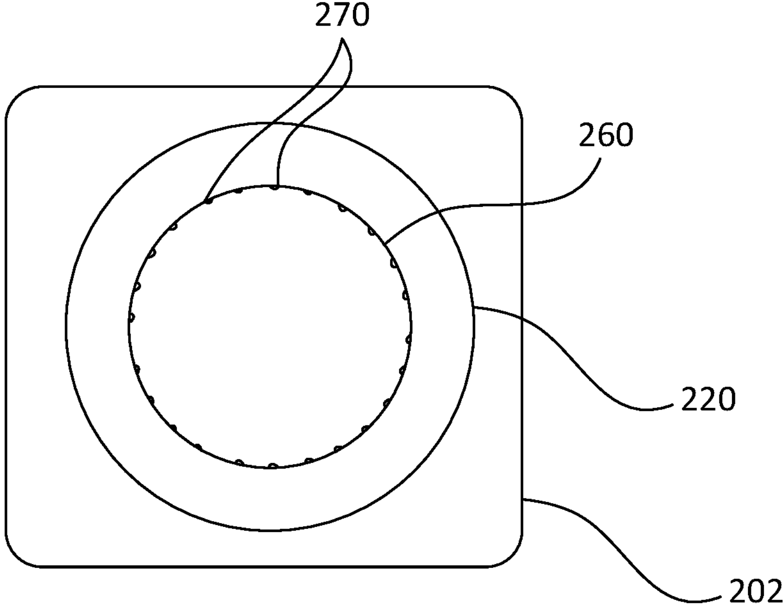

FIGS. 4A-B illustrates various cross-sections illustrating the rotatability of the arm portion of the electro-mechanical system. For example, in FIG. 4A the housing 202 has contained therein a rotational mechanism comprised of inner rotational component 260 that is press-fit and frictionally coupled to the outer rotational component 220. Another version of this is shown in FIG. 4B where additional detents 270 are added around a perimeter. Other alternatives include a gearing system, a slide and key-lock system and so forth. Rotational mechanisms come in various styles and these are provided by way of example.

It should be noted that the arm 120 can be configured to rotate with respect to an axis about the housing 102. This enables the dentist or other user of device 100 to be able to position the prongs on the desired injection site and navigate it such where the can see and operate the operation controls 130. Another feature that is helpful in the operating of the device 100 include the angled arm and prongs, which can be angled anywhere from 5 to 35 degrees. This allows the dentist to again pull back the side of the mouth, thus allowing them a better visual of the desired injection site, so they can clearly guide an injection needle in with their opposite.

The device 100 is designed to be operated with one hand, so that a user, such as a dentist can use an injection needle with their other hand. The rotatability and the angled prongs enable this.

Another benefit of the arm 120 is that it can be removed from the housing 102 to be cleaned. For example, the arm 120 can be detached and put in an autoclave, which is a common cleaning system used in dental and medical practices.

As noted above the electrical stimulation areas 124A, 124B can be formed of a different material from the rest of arm 120. For example, they could be formed of a metallic or other electrically conductive material, whereas the arm could be formed of a durable yet flexible plastic material.

It is desirable that the arm and forks be formed of a material that has sufficient rigidity to translate the vibrations generated from the vibratory system 110, which in most embodiments is disposed in the housing 102. It should be understood that the vibratory system 110 could also be included in the arm 120 and driven by controlling circuitry disposed in the housing 102.

Of course, the present invention is not limited to the above features and advantages. Those of ordinary skill in the art will recognize additional features and advantages upon reading the following detailed description, and upon viewing the accompanying drawings.

Figure 5:
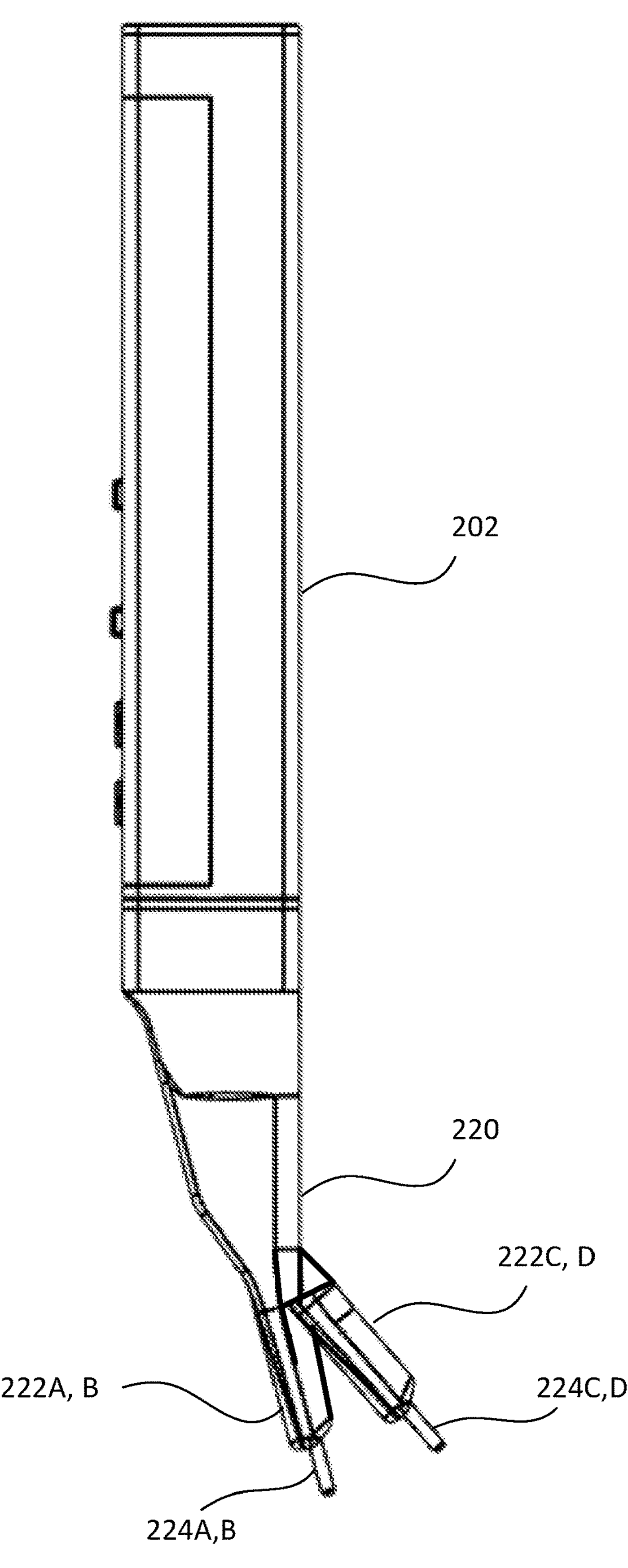
FIG. 5 illustrates an alternative embodiment including 4 prongs.

For example, FIG. 5 illustrates an alternative embodiment of an electro-mechanical device 200 having a housing 202 having an arm 220 extending therefrom that includes 4 prongs 222A-D, each having a conductive area 224A-D associated therewith. One of the advantages of the additional prongs is it establishes a perimeter about an injection site. Though 2 prong and 4 prong versions have been discussed, it is within the scope of this invention to include versions that have 3 prongs or more than 4 prongs.

Notably, modifications and other embodiments of the disclosed invention(s) will come to mind to one skilled in the art having the benefit of the teachings presented in the foregoing descriptions and the associated drawings. Therefore, it is to be understood that the invention(s) is/are not to be limited to the specific embodiments disclosed and that modifications and other embodiments are intended to be included within the scope of this disclosure. Although specific terms may be employed herein, they are used in a generic and descriptive sense only and not for purposes of limitation.

The invention claimed is:

1. An electro-mechanical system for preparing injection sites, the system comprising:

a housing;

a vibratory system disposed at least partially within the housing;

a power supply connected to the housing;

an arm having a first fork portion and a second fork portion;

an electrical stimulation system, wherein a portion of the electrical stimulation includes electrical stimulating areas disposed on each of the first and second fork portions; and a set of controls disposed on an outer surface of the housing, the set of controls in communication with a control circuitry for operating the vibratory system and the electrical stimulation system; and wherein the control circuitry is programmed to, upon activation, initiate a first vibratory frequency generated by the vibratory system, and then automatically subsequently initiate a first electrical stimulation frequency generated by the electrical stimulation system without deactivating the vibratory system.

2. The electro-mechanical system of claim 1, wherein the arm is connected to the housing by an arm housing, the arm housing comprising an inner rotational component, the first fork portion and second for portion connected to the inner rotational component, the inner rotational component rotatably connected to an outer rotational component formed by the arm housing, and wherein the first fork portion and second fork portion are operable to rotate relative to the housing by a rotation of the inner rotational component relative to the outer rotational component.

3. The electro-mechanical system of claim 1, wherein the set of controls are configured to increase or decrease the vibratory frequency of the vibratory system.

4. The electro-mechanical system of claim 1, wherein the set of controls are configured to increase or decrease the electrical stimulation frequency of the electrical stimulation system.

5. The electro-mechanical system of claim 1, wherein the set of controls are configured to cause the vibratory system to change from the first vibratory frequency to a second vibratory frequency.

6. The electro-mechanical system of claim 1, wherein the control circuitry is programmed to cause the electrical stimulation system to change from the first electrical stimulation frequency to a second electrical stimulation frequency.

7. The electro-mechanical system of claim 1, wherein the vibratory system is configured to generate a vibration amplitude in a range from 2G to 5G.

8. The electro-mechanical system of claim 7, whereby the generated vibration amplitude of the vibratory system is configured to impart at the first fork portion or second fork portion a vibration amplitude in the range of 1G to 4G.

9. The electro-mechanical system of claim 7, wherein the vibratory system can generate a frequency in the range of 50 Hz to 300 Hz.

10. The electro-mechanical system of claim 1, wherein the first electrical stimulation frequency can be pulsed at pulse width range of 180-280 μs.

11. The electro-mechanical system of claim 1, wherein the first electrical stimulation system can deliver between 0 and 2.5 Watts via the electrical stimulating areas disposed on each of the first and second fork portions.

12. The electro-mechanical system of claim 1, wherein the activation of the vibratory system and the electrical stimulation system inside a recipient's mouth is configured to cause A-beta fibers to activate, thus closing the pain gate from an oral cavity of the recipient's mouth to the recipient's central nervous system.

* * * * *